US008734761B2

(12) United States Patent
Willard et al.

(10) Patent No.: US 8,734,761 B2
(45) Date of Patent: May 27, 2014

(54) RESPONSIVE MRI CONTRAST AGENTS

(75) Inventors: Nicolaas Petrus Willard, Eindhoven (NL); Rene Theodorus Wegh, Eindhoven (NL); Jeroen Alphons Pikkemaat, Eindhoven (NL); Holger Gruell, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1408 days.

(21) Appl. No.: 11/912,694

(22) PCT Filed: Apr. 21, 2006

(86) PCT No.: PCT/IB2006/051235
§ 371 (c)(1),
(2), (4) Date: Oct. 26, 2007

(87) PCT Pub. No.: WO2006/114738
PCT Pub. Date: Nov. 2, 2006

(65) Prior Publication Data
US 2008/0193384 A1  Aug. 14, 2008

(30) Foreign Application Priority Data
Apr. 26, 2005  (EP) .................................. 05103356

(51) Int. Cl.
*A61B 5/055* (2006.01)

(52) U.S. Cl.
USPC ....................................... 424/9.3; 424/9.363

(58) Field of Classification Search
None
See application file for complete search history.

(56) References Cited

U.S. PATENT DOCUMENTS

| 19,878 | A | 4/1958 | Scoville | |
|---|---|---|---|---|
| 5,914,095 | A | 6/1999 | Watson | |
| 6,746,662 | B1 | 6/2004 | Sherry et al. | |
| 2002/0071843 | A1* | 6/2002 | Li et al. ...................... | 424/155.1 |
| 2002/0127182 | A1 | 9/2002 | Sherry et al. | |
| 2004/0030239 | A1 | 2/2004 | Van Zijl et al. | |
| 2004/0131551 | A1 | 7/2004 | Ranganathan | |
| 2004/0258614 | A1* | 12/2004 | Line et al. ................... | 424/1.11 |
| 2007/0009442 | A1 | 1/2007 | Platzek | |
| 2007/0014725 | A1 | 1/2007 | Platzek | |
| 2007/0036727 | A1* | 2/2007 | Aime et al. ................. | 424/9.32 |
| 2007/0292354 | A1* | 12/2007 | Port .......................... | 424/9.321 |

FOREIGN PATENT DOCUMENTS

| WO | 0047111 | 8/2000 |
|---|---|---|
| WO | 0066180 | 11/2000 |
| WO | 02/43775 | 6/2002 |
| WO | 03009874 A1 | 2/2003 |
| WO | 03013617 A2 | 2/2003 |
| WO | 03/063912 | 8/2003 |
| WO | 2004065385 | 8/2004 |
| WO | 2004089424 | 10/2004 |

OTHER PUBLICATIONS

Meade et al. (Curr. Opinion Neurobiol., 2003, 13, 597-602).*
Ladd et al. (Bioconj. Chem. 1999, 10, 361-370).*
Bulte et al. (NMR Biomed., 2004, 17, 484-499).*
Zhang S; Sherry A D: "Paramagnetic CEST Agents: Relaxation Versus Exchange", Proceedings of the International Society for Magnetic Resonance in Medicine, vol. 11, 2003, pp. 2514-2514, XP002422309.
Aime S, et al: "Paramagnetic Lanthanide(III) Complexes as pH-Sensitive Chemical Exchange Saturation Transfer (CEST) Contrast Agents for MRI Applications", Magnetic Resonance in Medicine, vol. 47, No. 4, 2002, pp. 639-648, XP001151918.
Aime S; Delli Castelli D; Fedeli F; Terreno E: "A Paramagnetic MRI—CEST Agent Responsive to Lactate Concentration", Journal of the American Chemical Society, American Chemical Society, vol. 124, No. 32, 2002, pp. 9364-9365, XP001151919.
K.M. Ward et al; "Determinatin of pH Using Water Protons and Chemical Exchange Dependent Saturation Transfer (CEST)", Magnetic Resonance in Medicine, vol. 44, pp. 799, 2000.
Nicholas Goffeney et al; "Sensitive NMR Detection of Cationic-Polymer-Based Genedelivery Systems Using Saturation Transfer Via Proton Exchange", Jour. Am. Chem. Soc., 2001, vol. 123, pp. 8628, 8629.
Eiichi Kimura et al; "A Tris (Zn 11-1, 4, 7, 10-Tetraazacycododecane) Complex as a New Receptor for Phosphate Dianiions in Aqueous Solution", Jour. Am. Chem. Soc. 1997, vol. 119, 3068-3076.
G.J.M. Koper et al; "Protonation Mechanism of Poly(Propylene Imine) Dendrimers and Some Associated Oligo Amines", Jour. Am. Chem. Soc. , 1997, vol. 119, 6512-6521.
Shanrong Zhang et al; "The Amide Protons of an Ytterbium (111) Dota Tetraamide Complex Act as Efficent Antennae for Transfer Ofmagnetization to Bulk Water", Angew. Chem. In. Ed. 2002, vol. 41, No. 11.
A. Heppeler et al; "Radiometal-Labelled Macrocyclic Chelator-Derivatised Somatostatin Analoguewith Superb Tumour-Targeting Properties and Potential for Receptor-Mediated Internal Radiotherapy", Chem Eur. J., 1999, vol. 5, No. 7.
Toth, Eva, et al "The Role of Water Exchange in Attaining Maximum Relaxivities for Dendrimeric MRI Contrast Agents", Chemical Engineering, vol. 2, No. 2, 1996.
Kobayashi, Hisataka, et al "Novel Liver Macromolecular MR Contrast Agent with a Polypropylenimine Diaminobutyl Dendrimer Core: Comparison to the Vascular MR Contrast Agent with the Polyamidoamine Dendrimer Core", Magnetic Resonance in Medicine, vol. 46, 2001, pp. 795-802.
Kobayashi, Hisataka, et al "Macromolecular MRI Contrast Agents with Small Dendrimers: Pharmacokinetic Differences between Sizes and Cores", Bioconjugate Chem. vol. 14, 2003, pp. 388-394.
Langerels, Sander et al "Multivalent Contrast Agents based on Gadolinium—Diethylenetriaminepentaacetic Acid-Terminated Poly(propylene imine) Dendrimers for Magnetic Resonance Imaging", Macromolecules, vol. 37, 2004, pp. 3084-3091.
Terreno, Enzo et al "Ln(III)-DOTAMGly Complexes: A Versatile Series to Assess the Determinants of the Efficacy of Paramagnetic Chemical Exchange Saturation Transfer Agents for Magnetic Resonance Imaging Applications", Investigative Radiology, vol. 39, No. 4, 2004, pp. 235-243.

* cited by examiner

*Primary Examiner* — Michael G Hartley
*Assistant Examiner* — Melissa Perreira (57) ABSTRACT

The invention provides MRI contrast agents which provide a high sensitivity and which have an optimised body retention time. These agents enable the mapping of the local pH, temperature, oxygen concentration or other metabolites in a patient's body by the use of Chemical Exchange Saturation Transfer (CEST). Particularly pH and temperature mapping are useful for the detection of small cancer lesions and localized inflammation respectively.

15 Claims, 12 Drawing Sheets

FIG.15

RESPONSIVE MRI CONTRAST AGENTS

The present invention relates to contrast agents for use in magnetic resonance imaging (MRI). More particularly, the invention relates to MRI contrast agents which enhance the sensitivity of the MRI technique and which have an optimised retention time in the body, and to a method for the preparation of such contrast agents.

Magnetic Resonance Imaging (MRI) is one of the major imaging techniques in medicine. In this technique, images are obtained by applying a strong magnetic field, a magnetic-field gradient, and frequency-matched RF pulses to a patient. During the imaging process, atomic nuclei in the body, which have a magnetic moment and which are mostly protons, become excited by the RF radiation. When the RF pulse is stopped, relaxation of the excited nuclei causes emission of an RF signal. As a result of applied magnetic-field gradients, the frequencies in this RF signal contain spatial information and can be used to construct an image. When the difference in intensity, i.e. the contrast between the different tissues is not sufficient to obtain satisfactory clinical information, MRI contrast agents are used. All currently used contrast agents possess permanent magnetic dipoles, which influence the relaxation process of the nearby water protons and so lead to a local change of the image contrast.

MRI is one of the main carriers for molecular imaging, a very promising new field which aims at the in-vivo characterisation of biological pathways. This will enable detection of diseases in a much earlier stage than at present. To achieve this, specially designed contrast agents are required, i.e. contrast agents that either bind with markers of the biological process to be studied and which are called targeted contrast agents, or contrast agents that give a different MR signal at the site of the biological process to be studied and which are called responsive, smart or sensor contrast agents. This difference in MR signal can be induced by a difference in e.g. pH, temperature, or metabolite concentration. The imaging of pH can, for example, enable detection of small cancer lesions, since the pH at such a site is lowered due to reduced buffering capacity and increased lactic acid production. Similarly, the mapping of temperature can detect sites of inflammation.

For, for example, pH mapping several methods are known. One is the use of a contrast agent of which the relaxivity depends on the pH. Another method is by using Chemical Exchange Saturation Transfer (CEST). By using the CEST technique, the image contrast is obtained by altering the intensity of the water signal, instead of differences in $T_1$, $T_2$ relaxation times. This is done by selectively saturating a pool of exchangeable protons using an RF pulse. These protons subsequently transfer the saturation to nearby water by exchange with water protons, thereby decreasing the water signal. The extent of water signal decrease depends on the proton exchange rate and on the concentration of the exchangeable protons. Since the proton exchange rate can depend on pH, this method enables pH mapping.

The possibility of pH mapping using CEST has been widely studied. For example, several small molecules with exchangeable protons have been investigated, but the CEST effect, i.e. the extent of water signal decrease, remained small even at high concentration of e.g. 62 mM [K. M. Ward and R. S. Balaban, Mag. Res. Med. 44,799, (2000)].

One way to improve the sensitivity of the CEST agent is by increasing the number of exchangeable protons per molecule. This follows from the fact that the total CEST effect, represented by the pseudo first-order exchange rate constant $k_1$, depends on the single exchange site rate constant $k_{CA}$ ($s^{-1}$) and on the total number of exchange sites available:

$$k_1 = k_{CA}[CA]n \quad (1)$$

wherein [CA] is the concentration of the contrast agent molecule and n is the number of chemical exchange sites per molecule. In order to increase $k_1$ by increasing n, a few macromolecules as CEST agent were studied. For example, poly-L-lysine having more than 2000 amide protons per molecule gave a significant CEST effect at 11 µM [N. Goffeney et al., J. Am. Chem. Soc. 123, 8628, (2001)]. However, the disadvantage of these macromolecules is that the chemical shift of the exchangeable protons with respect to the water signal is small, which makes selective saturation of these macromolecular protons instead of the water protons difficult. In fact, this can only be done if there is a discrete resonance frequency difference between water and the exchangeable protons, i.e. if the following equation holds:

$$(1/k_{CA})\Delta\omega_{CA} > 1 \quad (2)$$

wherein $\Delta\omega_{CA}$ is the chemical shift difference (rad/s) between water and the exchangeable protons. So the larger $\Delta\omega_{CA}$ is, the larger $k_{CA}$ and thus the CEST effect can be.

Figure 1:
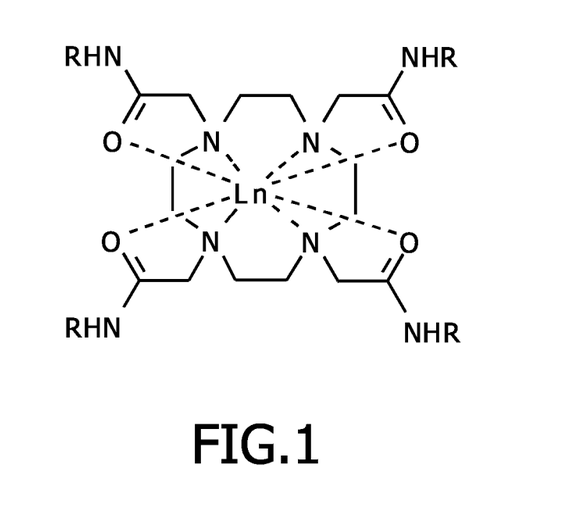
FIG. 1 illustrates a Ln-DOTAM complex used as a CEST agent according to the prior art.

It is known that chemical shifts of protons that are situated close to a paramagnetic ion, e.g. a lanthanide ion, can be very large. This has been exploited for CEST by Aime et al. who used lanthanide complexes of macrocyclic DOTAM derivatives (see FIG. 1) (DOTAM=1,4,7,10-tetraazacyclo-dodecane-1,4,7,10-tetraacetamide) ["Paramagnetic lanthanide (III) complexes as pH-sensitive chemical exchange saturation transfer (CEST) contrast agents for MRI applications", Magnetic Resonance in Medicine 2002, 47, p. 639]. The amide protons of these complexes proved to be suitable for pH mapping using CEST because of the strong pH dependence of the amide proton exchange. However, the number of exchangeable protons per molecule is limited to 8 at maximum. This leads to a sensitivity, defined as the concentration at which the CEST effect is 5%, in the order of 0.3 mM, i.e. a factor of 10 worse relative to standard Gd-based MRI contrast agents.

It is an object of the present invention to provide MRI contrast agents which enhance the sensitivity of the MRI technique and which have an optimised retention time in the body, and to a method for the preparation of such a contrast agent.

The above objective is accomplished by a method and device according to the present invention.

Particular and preferred aspects of the invention are set out in the accompanying independent and dependent claims. Features from the dependent claims may be combined with features of the independent claims and with features of other dependent claims as appropriate and not merely as explicitly set out in the claims.

The following terms are provided solely to aid in the understanding of the invention. These definitions should not be construed to have a scope less than understood by a person of ordinary skill in the art.

Chemical Exchange Saturation Transfer (CEST): refers to all saturation transfer processes that are dependent on chemical exchange between two molecules which exhibit different magnetic resonance frequencies.

CEST effect: extent of the decrease of the signal used to generate the MR image, caused by CEST, e.g. the water proton signal decrease in the case of proton imaging. The CEST effect can be written as $1-M_S/M_0^*$, wherein $M_S$ is the intensity of that signal upon pre-saturation of the exchangeable entities, e.g. exchangeable protons, and $M_0^*$ is the intensity of that signal upon irradiating at an off-resonance frequency, preferably at the opposite side of the frequency spectrum relative to that signal (symmetrical off-resonance).

CEST spectrum: the intensity of the signal used to generate the MR image, caused by CEST, e.g. the intensity of the water proton signal in the case of proton imaging, as a function of pre-saturation frequency offset.

CEST Contrast agent (CA): material having at least one exchangeable entity, e.g. proton, that can chemically exchange for exchangeable entities, e.g. protons, of another material, and which can be used to perform CEST imaging. The exchangeable entity, e.g. proton, may or may not be incorporated in an exchangeable molecule or group of atoms, e.g. a water molecule.

Exchangeable entity pool: the whole of all exchangeable entities which on the one hand chemically exchange with other exchangeable entities, e.g. protons, and on the other hand are chemically and magnetically equivalent. A specific example of an exchangeable entity pool may be an exchangeable proton pool.

Water proton signal: The signal in the proton NMR spectrum caused by the resonance of the protons of free water, the signal having a frequency and an intensity.

The present invention provides a MRI contrast agent comprising at least one CEST-active paramagnetic complex linked to a carrier, the at least one CEST-active paramagnetic complex comprising at least one exchangeable entity for enabling CEST.

According to embodiments of the present invention, the CEST-active paramagnetic complex may comprise a paramagnetic ion attached to a chelating ligand. The paramagnetic ion may for example be a lanthanide ion or any other paramagnetic ion such as a transition metal ion. The chelating ligand may be DOTAM or a DOTAM derivative (e.g. DOTAM with an R-group different from H, for example $COO^-$, $COOEt$, $PO_3^{2-}$, etc.). The paramagnetic complex may then, for example, be a Yb-DOTAM complex.

An advantage of the MRI contrast agent according to the invention is that a contrast agent having more than one type of proton pool can easily be obtained by attaching two different paramagnetic complexes to the same carrier.

According to embodiments of the invention, the paramagnetic complex may be covalently attached to the carrier. In that case, the carrier may be a dendrimer, for example a PPI dendrimer, or a linear polymer. In other embodiments, the paramagnetic complex may be non-covalently attached to the carrier. In these cases, the carrier may be a liposome or a particle such as a micell. The paramagnetic complex may in this case furthermore comprise a phospholipid tail.

In other embodiments according to the invention, the CEST-active paramagnetic complex may comprise superparamagnetic iron oxide (SPIO) particle embedded in an organic material.

According to a preferred embodiment of the invention, the MRI contrast agent may comprise:
at least one of a first CEST-active paramagnetic complex, the first CEST-active paramagnetic complex comprising a first paramagnetic ion, a first chelating ligand and at least one first exchangeable entity, and
at least one of a second CEST-active paramagnetic complex, the second CEST-active paramagnetic complex comprising a second paramagnetic ion, a second chelating ligand and at least one second exchangeable entity,
wherein at least one of the first and second paramagnetic ions, first and second chelating ligands and first and second exchangeable entities are different from each other.

According to embodiments of the present invention, the exchangeable entity may be a proton, a water molecule or a phosphate group. CEST may also be enabled by a water molecule bound to the paramagnetic ion. This means that in some cases CEST may be enabled by exchangeable entities which are not part of the chelating ligand.

The present invention furthermore provides a method for the preparation of a MRI contrast agent, the contrast agent comprising at least one CEST-active paramagnetic complex linked to a carrier, said at least one CEST-active paramagnetic complex comprising a paramagnetic ion attached to a chelating ligand and at least one exchangeable entity for enabling CEST, the method comprising:
providing at least one chelating ligand,
providing a carrier,
linking said chelating ligand to said carrier, and
forming a CEST-active complex between the at least one chelating ligand and at least one paramagnetic ion.

An advantage of the MRI contrast agent according to the invention is that a contrast agent having more than one type of proton pool can easily be obtained by attaching two different paramagnetic complexes to the same carrier.

In a preferred embodiment, the method may comprise:
providing at least one of a first chelating ligand and at least one of a second chelating ligand,
providing a carrier,
linking said at least one first chelating ligand and said at least one second chelating ligand to said carrier, and
forming a complex having at least one first exchangeable entity between said at least one first chelating ligand and a first paramagnetic ion and a complex having at least one second exchangeable entity between said at least one second chelating ligand and a second paramagnetic ion,
wherein at least one of the first and second paramagnetic ions, first and second chelating ligands or first and second exchangeable entities respectively are different from each other.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

In the different figures, the same reference signs refer to the same or analogous elements.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

The present invention provides a contrast agent suitable for use in magnetic resonance imaging (MRI), and more particularly, a chemical exchange saturation transfer (CEST) contrast agent that provides a high sensitivity to the CEST MRI technique and that has an optimised retention time in the body. The present invention furthermore provides a method for the preparation of such contrast agents.

According to the invention, the MRI contrast agent comprises at least one CEST-active complex attached to a carrier. With CEST-active complex is meant a complex comprising at least one exchangeable entity such as e.g. a proton, a water molecule or a phosphate group for enabling CEST.

According to embodiments of the present invention, the CEST-active complex may comprise a paramagnetic ion attached to a chelating ligand. The paramagnetic ions may be lanthanides ions, e.g. ytterbium (Yb) ions, or any other suitable paramagnetic ions such as e.g. transition metal ions. Preferably, the paramagnetic ions may be lanthanide ions, more preferably the paramagnetic ions may be $Yb^{3+}$ ions. The chelating ligands form a complex with the paramagnetic ions.

In other embodiments according to the present invention, the paramagnetic complex may also be formed of a superparamagnetic iron oxide (SPIO) particle that is embedded in an organic material such as, for example, a polymer. For body compatibility, the superparamagnetic iron particles need to have a polymer shell. To be useful as CEST agent, the polymer shell should comprise exchangeable entities, for example exchangeable protons.

According to the invention, the paramagnetic complex comprises exchangeable entities, such as, for example, a proton, a water molecule or a phosphate group. Preferably, the exchangeable entity may be an exchangeable proton and more preferably, the exchangeable entity may be an exchangeable amide proton. The chelating ligands may, for example, be DOTAM or derivatives thereof (DOTAMs with R groups (see FIG. 1) different from H e.g. $COO^-$, COOEt, $PO_3^{2-}$, etc.).

The contrast agent according to the invention furthermore comprises a carrier to which the at least one CEST-active paramagnetic complex is linked. Linking may be done covalently, i.e. forming a polymer, or non-covalently, i.e. in the form of e.g. a liposome or a micelle.

An advantage of the paramagnetic complexes being attached to a carrier is that the pH range over which a big change in CEST effect occurs can be optimised by the choice of functional groups in the carrier. For example, when a CEST-active moiety or complex is attached directly to e.g. a PPI dendrimer, the pH-range exhibiting the big change in CEST effect shifts to lower pH because the PPI dendritic core is basic due to the many amine groups present.

Figure 2:
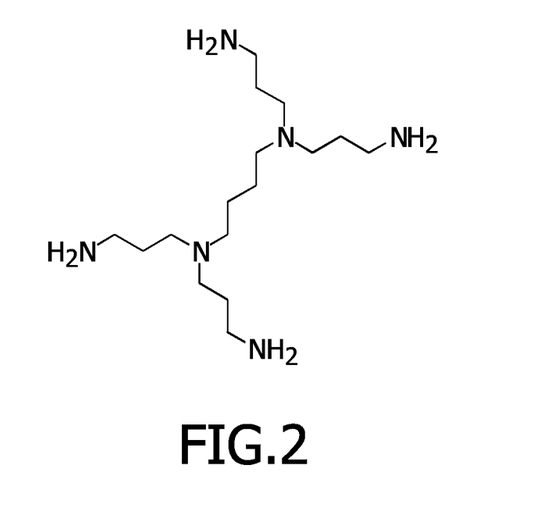
FIG. 2 shows a generation 1 (G1) poly(propylene imine) dendrimer.
Figure 3:
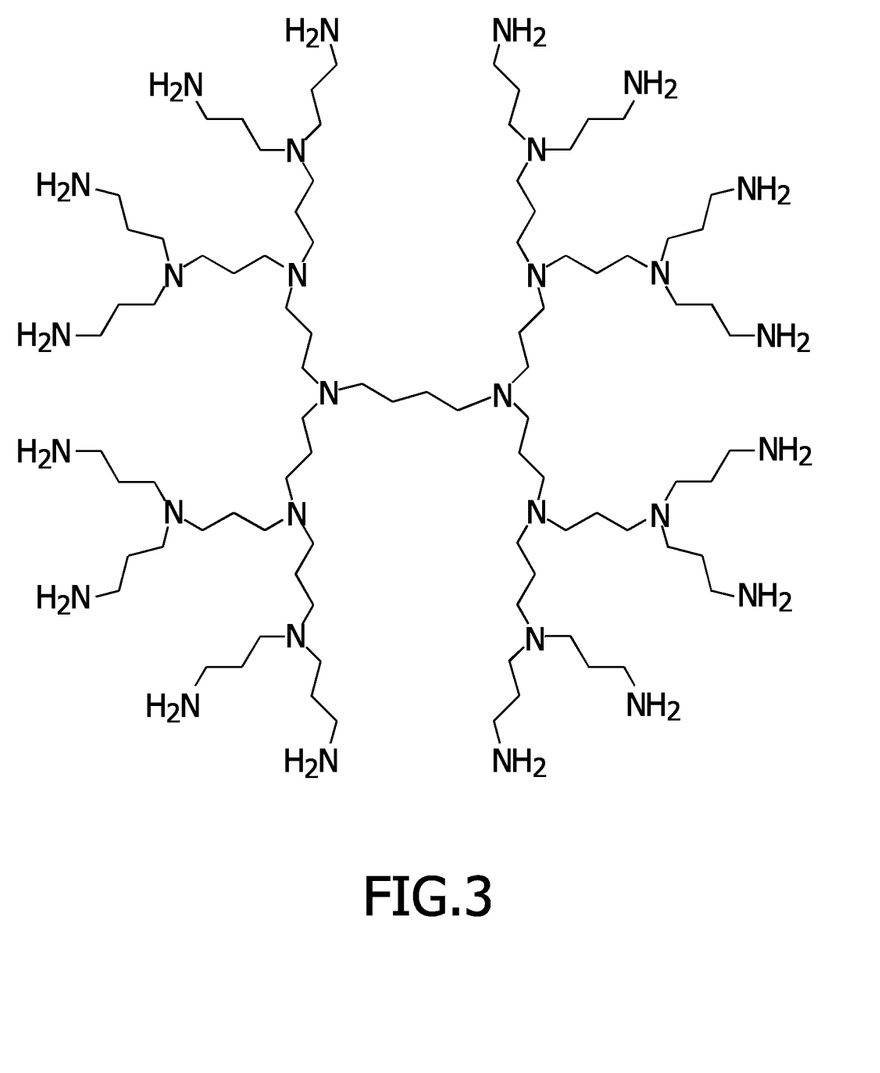
FIG. 3 shows a generation 3 (G3) poly(propylene imine) dendrimer.

In the case of covalently linking, different types of polymers, such as, for example, a dendrimer or a linear polymer may be used. A dendrimer may have the advantage over a linear polymer of having a controlled size and shape and therefore a well-defined bio-distribution. For example, for a dendrimer having amine end groups, these amine end groups can easily be functionalised with paramagnetic complexes. Another advantage of using a dendrimer as a carrier is that the size of the dendrimer, and therefore the body retention time, can be optimised by choosing the generation, because the bigger the contrast agent molecules are, the higher the body retention time in the body will be. As an illustration, a generation 1 or G1 poly(propylene imine) or PPI dendrimer, i.e. a PPI dendrimer with 4 end groups, is illustrated in FIG. 2 and a generation 3 or G3 PPI dendrimer, i.e. a PPI dendrimer with 16 end groups, is illustrated in FIG. 3.

In other embodiments, a linear polymer may be used as a carrier. This may have the advantage with respect to dendrimers of better extravasation, i.e. escape of the CEST contrast agent from the blood vessels, into the tissue. Since the pores in the endothelium are about 10 to 20 nm, extravasation of particles or molecules with a molecular weight larger than 20 kDa is difficult. In this size range, linear polymers will pass the endothelium faster than bulky dendrimers.

In further embodiments of the invention, the carrier may be a liposome or a particle such as a micelle. In this case, the paramagnetic complex may comprise a paramagnetic ion which may be any paramagnetic ion as described above, a chelating ligand which may also be any chelating ligand as described earlier and a phospholipid tail. A phospholipid is a molecule comprising a hydrophilic head group, e.g. a phosphate group, and a lipophilic tail, e.g. one or more fatty acids, possibly saturated. Examples of such phospholipids may be e.g. 1,2-dilauroyl-, -dimyristoyl-, -dipalmitoyl-, -distearoyl-sn-glycero-3-phosphocholine or -phosphoethanolamine. A phospholipid may in addition comprise a poly(ethylene glycol) chain attached to the hydrophilic head group. The goal of the tail is to incorporate the complex into the shell of the liposome or particle. If the complex is included in the core, the tail is not used. The paramagnetic complex may be in the shell of the liposome or particle by covalently attaching the paramagnetic complex to the hydrophilic side of the phospholipid, or it may be included in the core of the liposome or particle.

Because a CEST agent according to the present invention may comprise a plurality of paramagnetic complexes attached to a carrier, such as e.g. a dendrimer, a linear polymer or a liposome, it may comprise a high number of exchangeable entities, e.g. exchangeable protons, exchangeable water molecules or exchangeable phosphate groups, with a resonance frequency well away from the resonance frequency of the main naturally present pool, i.e. the pool that is used to generate the image, which is water in the case of proton MRI.

An advantage of a carrier comprising a plurality of paramagnetic complexes is that a contrast agent comprising at least two different exchangeable entity pools, for example at least two different proton pools, can easily be provided by using at least two different paramagnetic complexes, each having different exchangeable entity pools, e.g. proton pools, and being attached to one and the same carrier. For example, in the prior art, concentration dependence has been eliminated by Aime et al. by using a cocktail of two CEST agents, i.e. an Yb complex using the amide proton exchange for CEST and a Eu complex using the water exchange ["Paramagnetic lanthanide(III) complexes as pH-sensitive chemical exchange saturation transfer (CEST) contrast agents for MRI applications", Magnetic Resonance in Medicine 2002, 47, p. 639]. Equal bio-distribution of the two molecules had to be assumed. According to the present invention, in the case of a carrier such as a polymer or a liposome or particle comprising a plurality of paramagnetic complexes, the two different CEST-active complexes, e.g. two different lanthanides, may be present on one particle/molecule at a fixed concentration ratio. In this way no assumption of equal bio-distribution needs to be made.

If two different paramagnetic complexes, i.e. first and second paramagnetic complexes, are attached to a same carrier, they may comprise different chelating agents and/or different paramagnetic ions. The carrier may comprise a plurality of first paramagnetic complexes and a plurality of second paramagnetic complexes.

Hereinafter, some examples of MRI contrast agents according to the different embodiments of the invention will be described in detail.

A first example of a CEST agent according to the present invention may comprise a PPI dendrimer as a carrier with a plurality of ytterbium(Yb)-DOTAM complexes attached to it. Therefore, an asymmetric DOTAM derivative was synthesised and coupled to the end groups of a PPI dendrimer generation 1 and 3 (see respectively FIG. 2 and FIG. 3). Thus, two different contrast agents may be obtained, i.e. Yb-DOTAM-G1 and Yb-DOTAM-G3. As a reference CEST agent, for comparison reasons only (see below), the asymmetric Yb-DOTAM complex was also coupled to an aliphatic/aromatic "tail", leading to the contrast agent further called Yb-DOTAM-tail.

Figure 4:
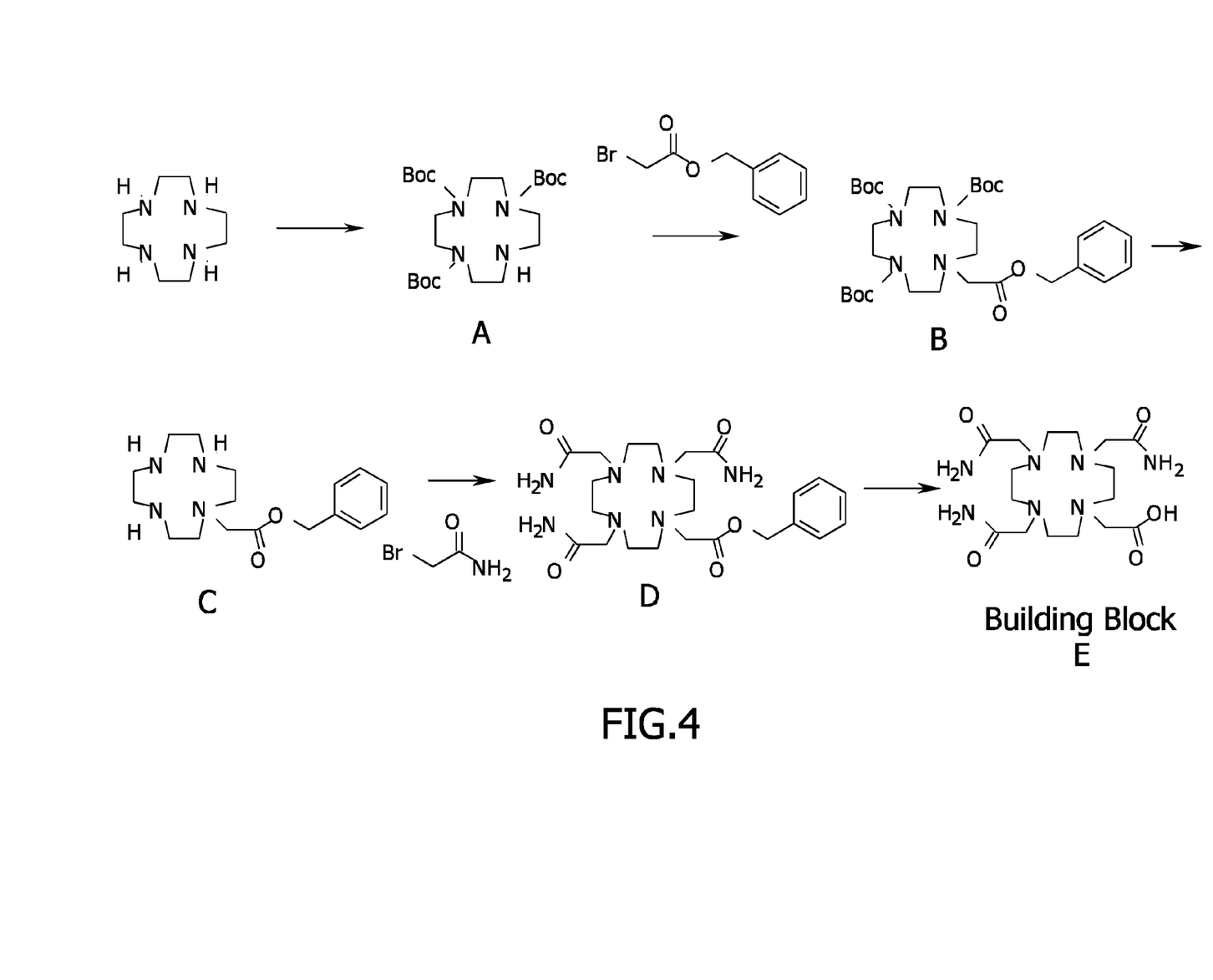
FIG. 4 to FIG. 6 illustrate the synthesis of Yb-DOTAM-tail, Yb-DOTAM-G1 and Yb-DOTAM-G3.

Lanthanide complexes of the three compounds may be obtained as follows. The synthesis of the 'building block' or paramagnetic complex is illustrated in FIG. 4. The synthesis is started from cyclen, which is a commercially available compound e.g. from Aldrich or Macrocyclics. The molecules A, B and C in FIG. 4 are known from the literature. Molecule A and its synthesis have been reported in a.o. "E. Kimura, J. Am. Chem. Soc., 1997, 199, 3068-3076". Molecule B has been reported in WO 2004065385, Molecule C has been reported in "A. Heppeler et al., Chem. Eur. J. 1999, 5, 7, 1974-1981".

Molecule A can be prepared by slowly, i.e. within 3 hours, adding a solution of di-tert-butyl dicarbonate (7.9 g, 36 mmol) in $CHCl_3$ (100 mL, passed through $Al_2O_3$) to a solution of cyclen (2.2 g, 13 mmol) and triethylamine (5.5 mL, 39 mmol) in $CHCl_3$ (120 mL) at room temperature. The reaction mixture is stirred for 24 hours at room temperature, and the organic solvent is removed under reduced pressure. The remaining residue is purified by silica gel column chromatography (hexanes/AcOEt) to provide molecule A as a colourless, amorphous solid (4.4 g, 72%)[ E. Kimura, J. Am. Chem. Soc., 1997, 199, 3068-3076].

The tri-BOC protected molecule A (15.2 g) is then dissolved in 20 mL of acetonitrile, after which 19 mL of diisopropylethylamine and 7.9 g of benzylbromoacetate in 10 mL acetonitrile are added. The solution is heated up to 60-65° C. and stirred overnight under an argon atmosphere. The mixture is then concentrated by evaporation of the solvent and dissolved in dichloromethane. The solution is washed with 1 M NaOH. The organic layer is dried with $Na_2SO_4$ and thereafter reduced by evaporation and co-evaporation with toluene. The pure product, molecule B, is isolated by silica column chromatography using hexane/ethyl acetate(1/1) as eluent. The yield is about 90%.

Molecule B (6.22 g) is dissolved in 60 mL dichloromethane and 60 mL trifluoracetic acid (TFA). The solution is stirred under a nitrogen atmosphere. After 3 hours the solvents are evaporated and another portion of TFA (40 mL) is added. After 2 hours of further stirring the TFA is evaporated and the remaining mixture is co-evaporated twice with toluene, leaving the crude TFA-salt of molecule C as an oil, of which then 10 g is used in a following step without further purification. The oil is dissolved and stirred in 45 mL DMF and 31 mL diisopropylethylamine. Then, 4.7 g bromo acetamide is added and the mixture is stirred for two days at 50° C., during which time a precipitate is developed. The mixture is brought in 600 mL ether, is stirred and the brown precipitate is isolated by filtration and washing with ether. The solid is then washed four times with portions of 25 mL of 25% $NH_3$ solutions in water and finally with 30 mL of water. Drying under vacuum at 40° C. results in a white solid product of molecule D (yield=85%).

Molecule D (1.7 g) is then hydrogenated at 70 psi overpressure in 100 mL water using Pd/C (10%) as catalyst. The mixture is filtered over celite, the celite is washed with some water and the filtrate is freeze dried and then dried over $P_2O_5$ in vacuum to afford 1.1 gram of a fine white hygroscopic powder of molecule E.

Figure 5:
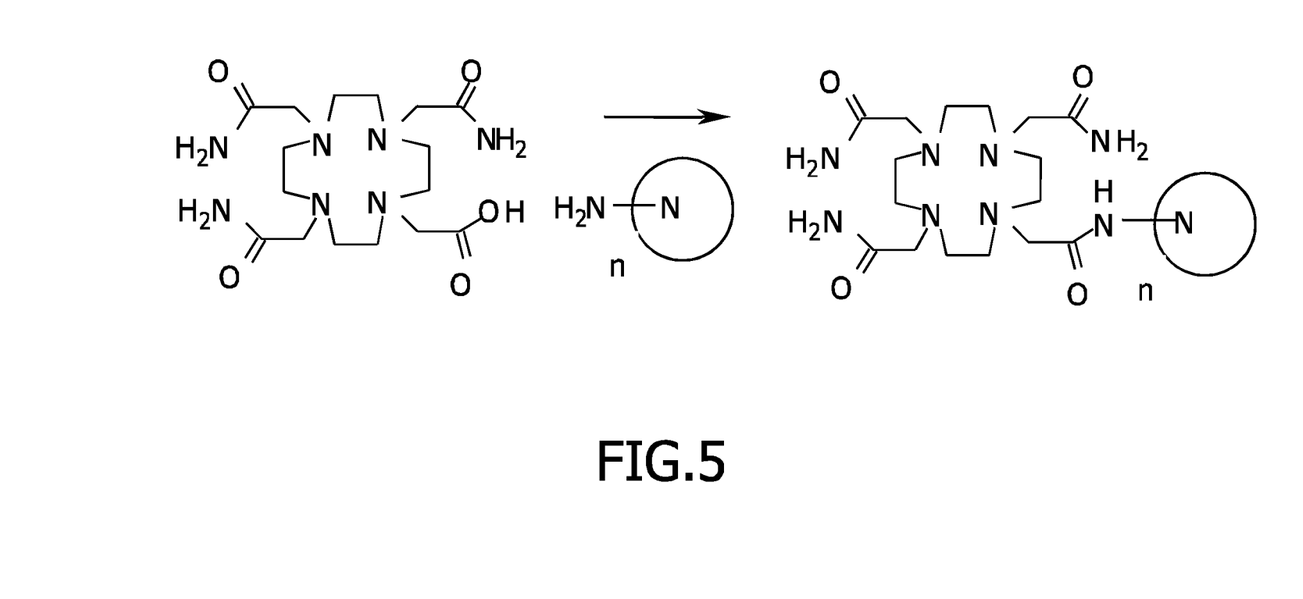

For the coupling of molecule E to the carrier, in the example given to a PPI dendrimer, the amide coupling agent HBTU (O-(benzotriazol-1-yl)-N,N,N',N'-tetramethyluronium hexafluorophosphate) is used. The coupling of the paramagnetic complex to the dendrimer is illustrated in FIG. 5. For convenience, the dendrimers are denoted as circles. The dendrimers used are commercially available poly(propylene imine) (PPI) dendrimers (from Aldrich under the name DAB-Am-X or from SyMO-Chem) with a diaminobutane (DAB) derived core. The most used name for those dendrimers is DAB-Am-X, wherein X refers to the number of surface amino groups. In this synthesis, DAB-Am-4 and DAB-Am-16 have been used in order to respectively obtain a DOTAM-G1 complex and a DOTAM-G3 complex. The formation of DOTAM-G1 and DOTAM-G3 is similar, only the value for the number n of end groups is different, i.e. for DOTAM-G1 n=4 and for DOTAM-G3 n=16.

For the coupling of molecule E to the G1 PPI dendrimer, 0.39 mL diisopropylethylamine is added to a mixture of 312 mg HBTU in 3 mL dry DMF. Molecule E (300 mg) is added, the mixture is stirred until a clear solution is acquired. This may take about 5 to 10 minutes. Subsequently, 60 mg DAB-Am-4 in 3 mL DMF is added. The mixture is stirred overnight under an inert atmosphere, after which it is dropped into 150 mL of ether. The sticky precipitate is taken up in a small amount of methanol and precipitated into ether giving a white solid, that is again precipitated from methanol into ether. Finally, the solid is dissolved in methanol and eluted over an anion exchange column (Dowex OH⁻). Evaporation of the solvent gave about 200 mg of product, which in the further synthesis will be called molecule II.

For the coupling of molecule E to the G3 PPI dendrimer, 0.25 mL diisopropylethylamine is added to a mixture of 164 mg HBTU in 1 mL dry DMF. Molecule E (172 mg) is added and the mixture is stirred until a clear solution is acquired. This may take about 5 to 10 minutes. The third generation PPI-dendrimer DAB-Am-16 (41 mg) in 1 mL dry DMF is then added and the solution is stirred overnight under an inert atmosphere of nitrogen. The mixture is poured into 40 mL of stirred ether giving a precipitate; the ether is replaced by another portion of ether (washing step), and the precipitate is dried. Finally, the precipitate is dissolved in water and triethylamine and this solution is dialysed using a membrane with a molecular weight cut-off of 1000 and using 1.2 L of water and 20 mL of triethyl amine as washing solvent. After overnight dialysis, the washing solution is replaced by 1.2 L of water and dialysis is continued for another 24 hours. Freeze drying of the solution in the dialysis tube gave ca. 200 mg of a fluffy white product, which in the further synthesis will be called molecule III.

Figure 6:
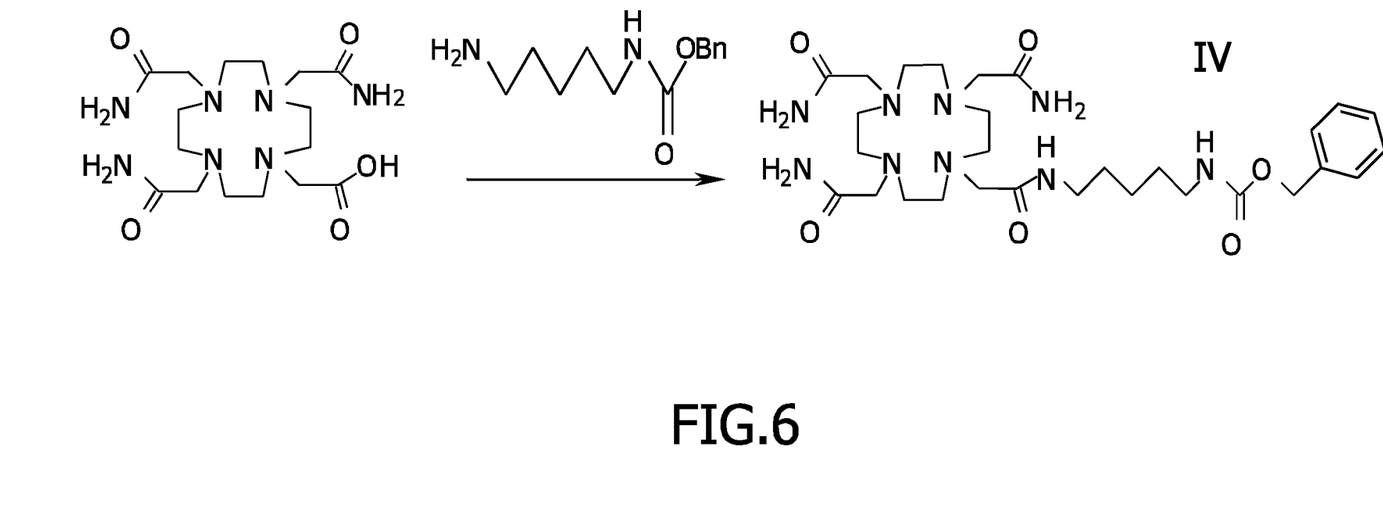

FIG. 6 illustrates the coupling of molecule E to an aliphatic/aromatic tail. A similar synthetic and purification procedure as used for molecule II may be applied, using N-carbobenzoxy-1,5-diaminopentane (mono Cbz-protected 1,5-pentyldiamine) as amine starting product. The resulting product will in the further synthesis be referred to as molecule IV.

A last step in the synthesis is the complexation with Yb³⁺ ions. For the formation of the Yb-DOTAM-G1 complex, a solution of 0.1 mmol YbCl₃ in 5 mL water is added dropwise to a stirring solution of 49 mg (0.1 mmol) of molecule II in 8 mL water. Subsequently, the solution is heated up to 60° C. for 2 hours while stirring, meanwhile maintaining a pH of 7 to 8 by adding small drops of NH₄OH. The solution is dialysed for 24 hours using a membrane with a molecular weight cut-off of 500 and running water as washing solvent. Freeze drying of the solution yields a white powder in a yield of ~80%.

For the formation of the Yb-DOTAM-G3 complex the complexation procedure is similar as for the Yb-DOTAM-G1 complex, but now molecule III is used instead of molecule II.

For the formation of the Yb-DOTAM-tail complex, the complexation procedures is also similar as for the Yb-DOTAM-G1 complex but now molecule IV is used instead of molecule II and a dialysis membrane with a molecular weight cut-off of 100 is used.

It has to be understood that the above-described synthesis may also be used to form other CEST contrast agents comprising, for example, other lanthanides than Yb or derivatives of the DOTAM chelating ligand.

Figure 7:
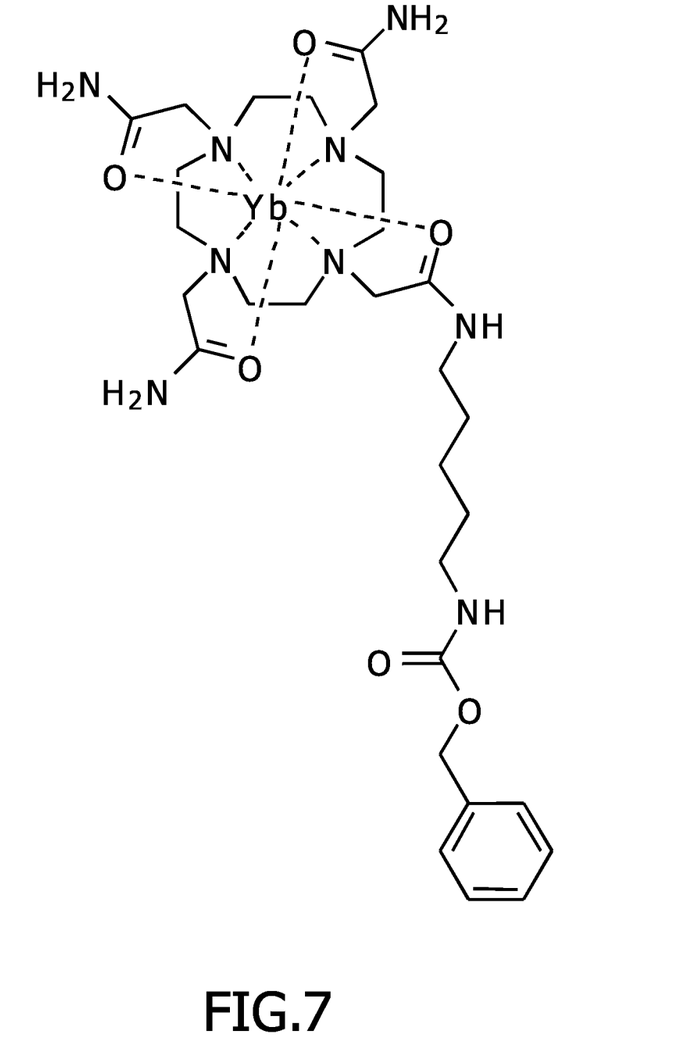
FIG. 7 illustrates an Yb-DOTAM-tail molecule used as a reference CEST agent in embodiments according to the present invention.
Figure 8:
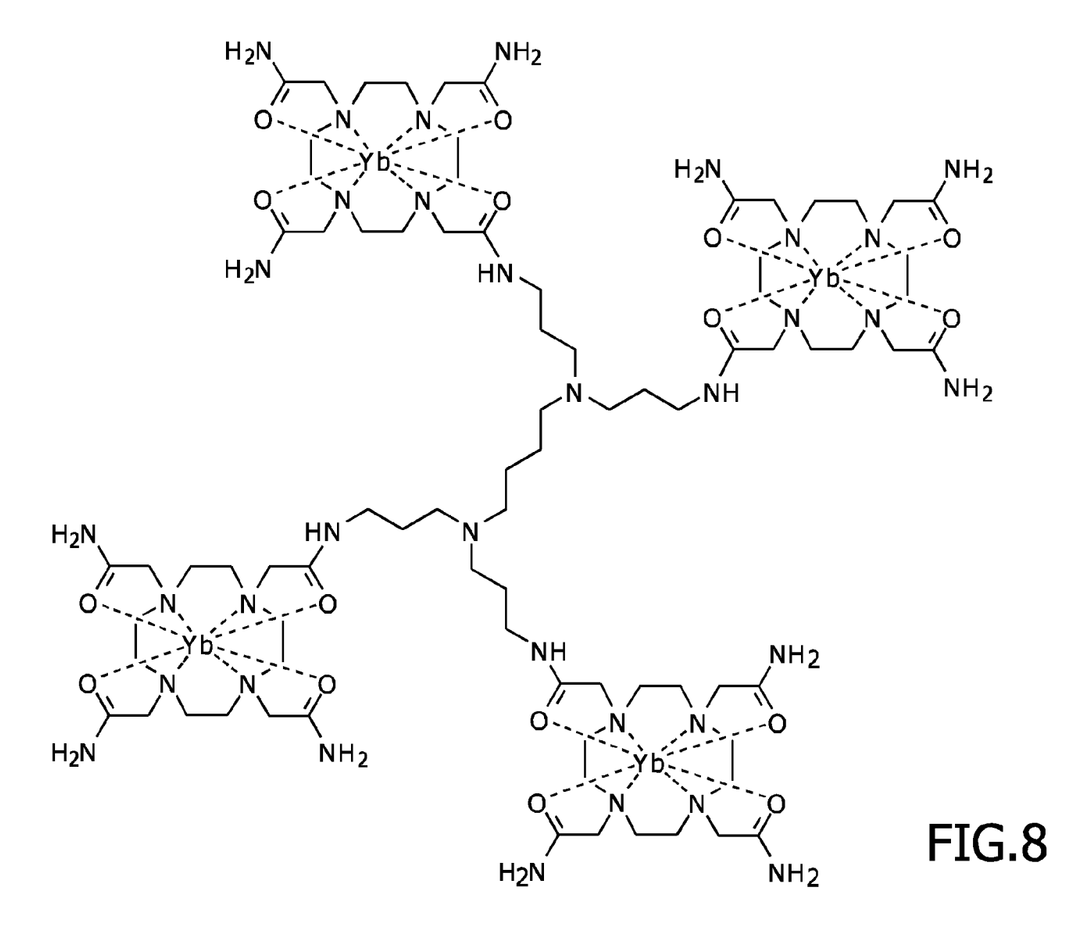
FIG. 8 illustrates a generation 1 (G1) poly(propylene imine) dendrimer functionalised with DOTAM groups.
Figure 9:
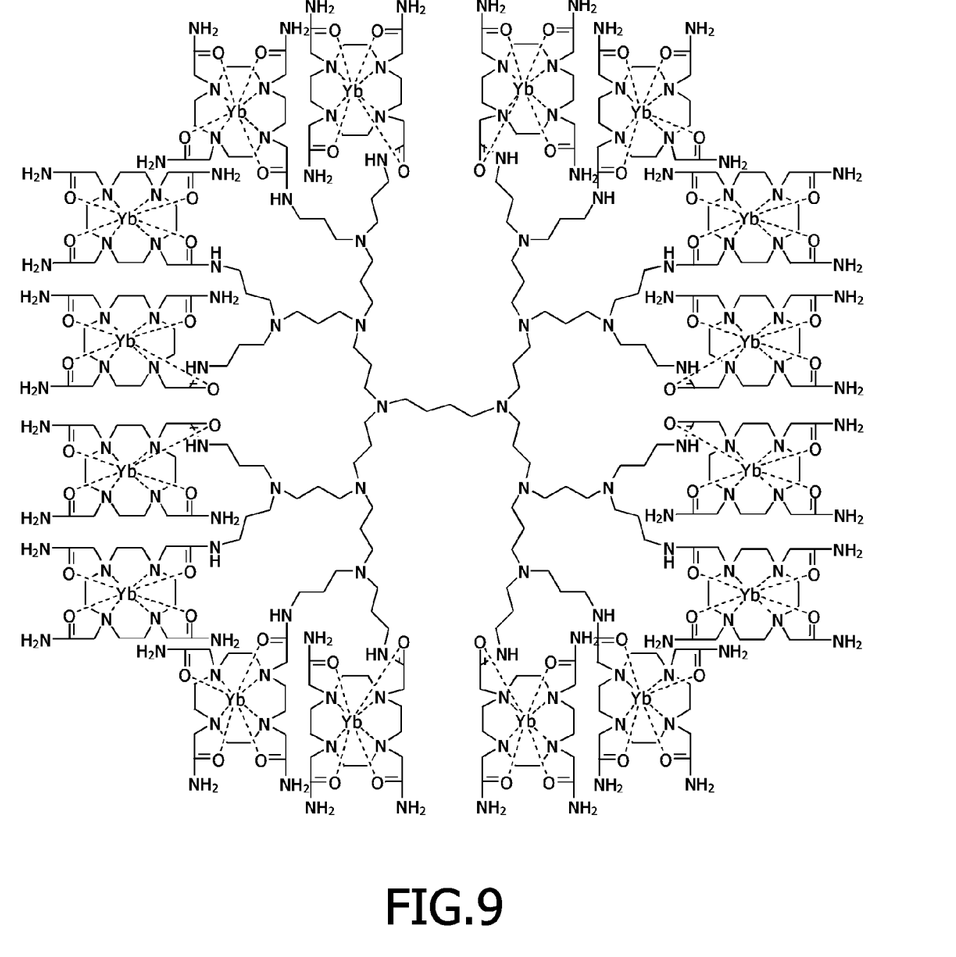
FIG. 9 illustrates an Yb-DOTAM-G3 CEST agent according to an embodiment of the invention.

The above synthesis thus results in the complexes Yb-DOTAM-tail (see FIG. 7), Yb-DOTAM-G1 (see FIG. 8) and Yb-DOTAM-G3 (see FIG. 9). In FIGS. 7 to 9 Yb represents Yb³⁺ and a water molecule is present at the 9ᵗʰ coordination site, which is omitted in the figures for the sake of clarity.

Figure 10:
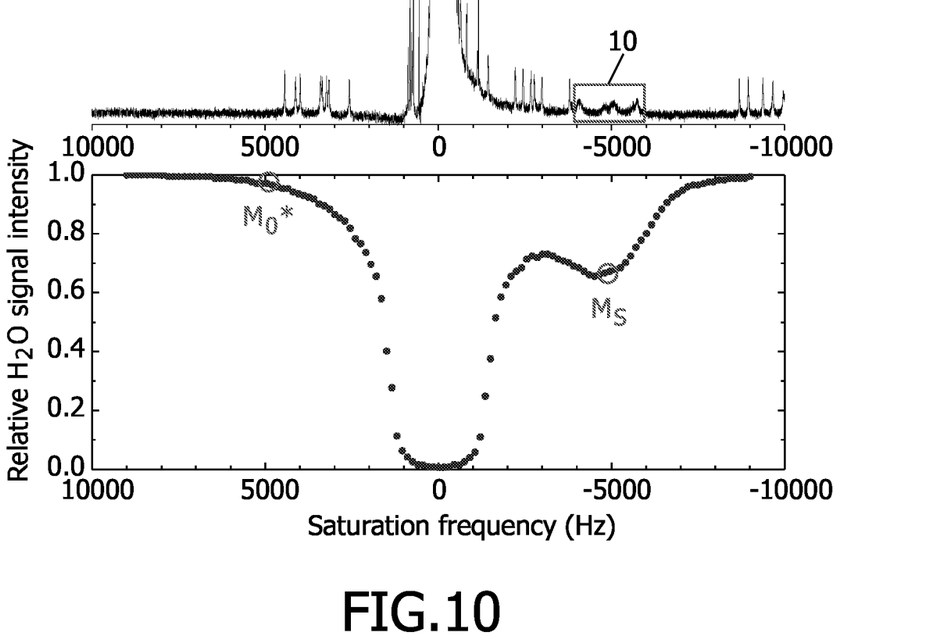
FIG. 10 shows a $^1$H-NMR spectrum (top) and a CEST spectrum (bottom) for Yb-DOTAM-tail (18 mM) with MOPS buffer in water at pH=7.05.

CEST experiments with the above-described Yb-DOTAM complexes attached to either a tail, a G3 PPI dendrimer or a G1 PPI dendrimer may be performed on a 7T Bruker NMR spectrometer. The CEST spectrum, i.e. the intensity of the signal used to generate the MR image, in the example given the water signal, as a function of the pre-saturation frequency offset for a solution of the Yb-DOTAM-tail contrast agent (18 mM) with a 3-morpholinopropanesulfonic acid (MOPS) buffer having formula:

is shown in FIG. 10. From this figure it can be seen that the intensity of the signal used to generate the MR image, in the example given the water signal intensity, goes to 0 upon pre-saturating the water protons directly, i.e. at 0 Hz. More important, a clear local minimum in the intensity of the signal used to generate the MR image, in the example given the water signal intensity, is obtained when irradiating at −5000 Hz frequency offset with respect to the water resonance, i.e. upon pre-saturating the amide protons (indicated by reference number 10 in the top graph of FIG. 10). In the example given, this intensity decrease is caused by the chemical exchange of the amide protons with the water protons.

The CEST Effect is Defined as:

$$\text{CEST effect} = 1 - M_S/M_0^* \quad (3)$$

wherein $M_S$ is the intensity of the signal used to generate the MR image, in the example given, the water signal intensity, upon pre-saturation of the exchangeable protons (−5000 Hz) and $M_0^*$ is the intensity of the signal to generate the MR image, in the example given, the water signal intensity, upon irradiating at the opposite side relative to the signal used to generate the MR image, in the example given, the water proton signal (+5000 Hz).

Figure 11:
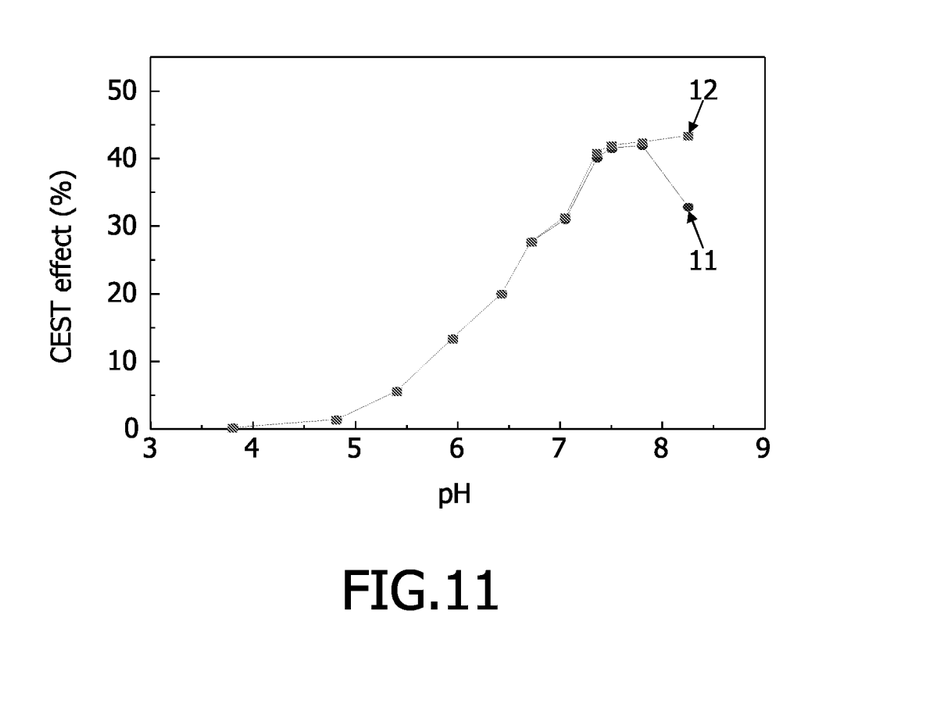
FIG. 11 illustrates the CEST effect as a function of pH for Yb-DOTAM-tail (18 mM) with MOPS buffer in water for a fixed RF pulse and for an optimised RF pulse.

FIG. 11 shows how the CEST effect varies with pH for Yb-DOTAM-tail complexes. The exchange of the amide protons is base-catalysed. Therefore, no CEST effect occurs at low pH. From FIG. 11 it can be seen that, in the case of an Yb-DOTAM-tail complex, CEST effect starts to take place from ~pH 5, and the CEST effect increases rapidly to ~42% at pH 7.5. The steep and gradual increase of the CEST effect in the clinically relevant pH range of 6.5-7.5 enables pH mapping with this material. At higher pH the CEST effect decreases again (curve 11 in FIG. 11) because the exchange gets so fast that the amide proton resonance merges with the water resonance, hampering selective pre-saturation of the amide protons (and not the water protons). Because of the shift of the amide proton resonance, at higher pH the maximum CEST effect is obtained when the irradiation frequency is shifted as well i.e. when the RF pulse is optimised (curve 12 in FIG. 11).

Figure 12:
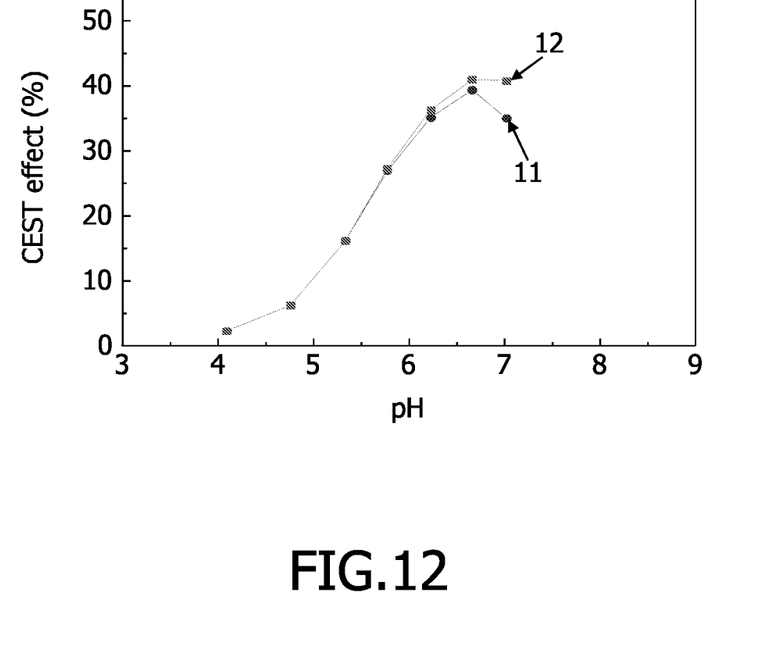
FIG. 12 illustrates the CEST effect as a function of pH for Yb-DOTAM-G3 (1.1 mM) with MOPS buffer in water for a fixed RF pulse and for an optimised RF pulse.

For the Yb-DOTAM-G3 complex a similar CEST-pH curve is obtained (see FIG. 12). The maximum CEST effect is again ~42% as expected because the concentration of the Yb-DOTAM-G3 complex was chosen to be 16 times smaller than for the Yb-DOTAM-tail complex i.e. the concentration of Yb and thus the concentration of amide protons was equal. The only difference is that the curve in FIG. 12 has shifted to lower pH compared to the curve for the Yb-DOTAM-tail complex (FIG. 11). This may be explained by the fact that the dendritic core is basic due to the tertiary amines [G. J. M. Koper et al., J. Am. Chem. Soc. 119, 6512 (1997)] and because the amide proton exchange is base-catalysed the exchange starts to occur at lower pH. Although the sharp increase in the CEST effect is now outside the clinically relevant pH range, it will be shown below that Yb-DOTAM-G3 can still be used for pH mapping.

Figure 13:
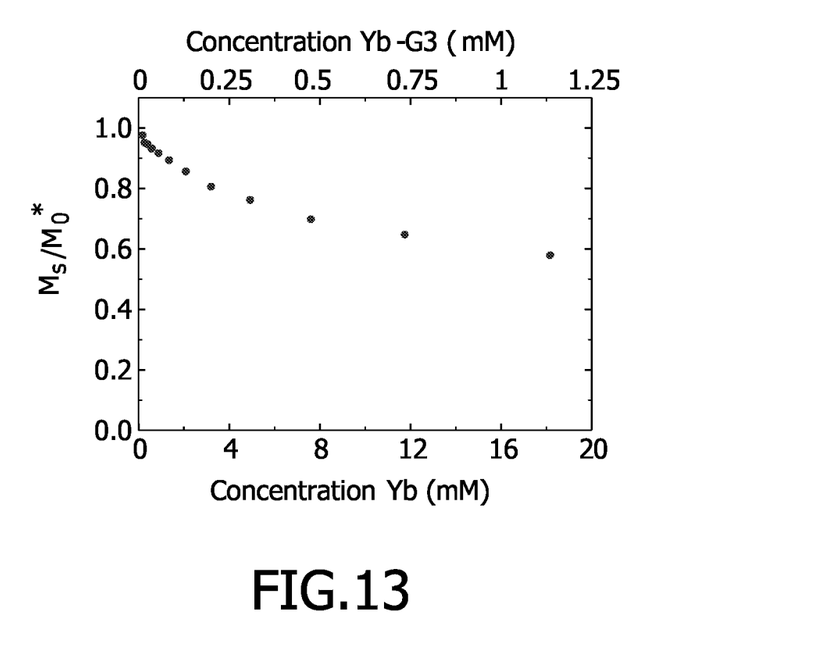
FIG. 13 illustrates the relative water signal intensity as a function of the concentration of Yb and Yb-DOTAM-G3.

The solution of the Yb-DOTAM-G3 complex with MOPS buffer in water was gradually diluted in order to study the concentration dependence of the CEST effect. As expected from theory [S. Zhang et al., Angew. Chem. Int. Ed. 41, 1919 (2002)], the intensity of the signal used to generate the MR image, in the example given the water signal intensity, increases, i.e. the CEST effect decreases, nonlinearly with decreasing concentration (see FIG. 13). The concentration at which the CEST effect is 5% may generally be used as a measure for the sensitivity. In the example given, this is ~20 µM for the Yb-DOTAM-G3 complex, a value comparable with the sensitivity of the common $T_1$ contrast agent Gd-DTPA (Magnevist™).

Figure 14:
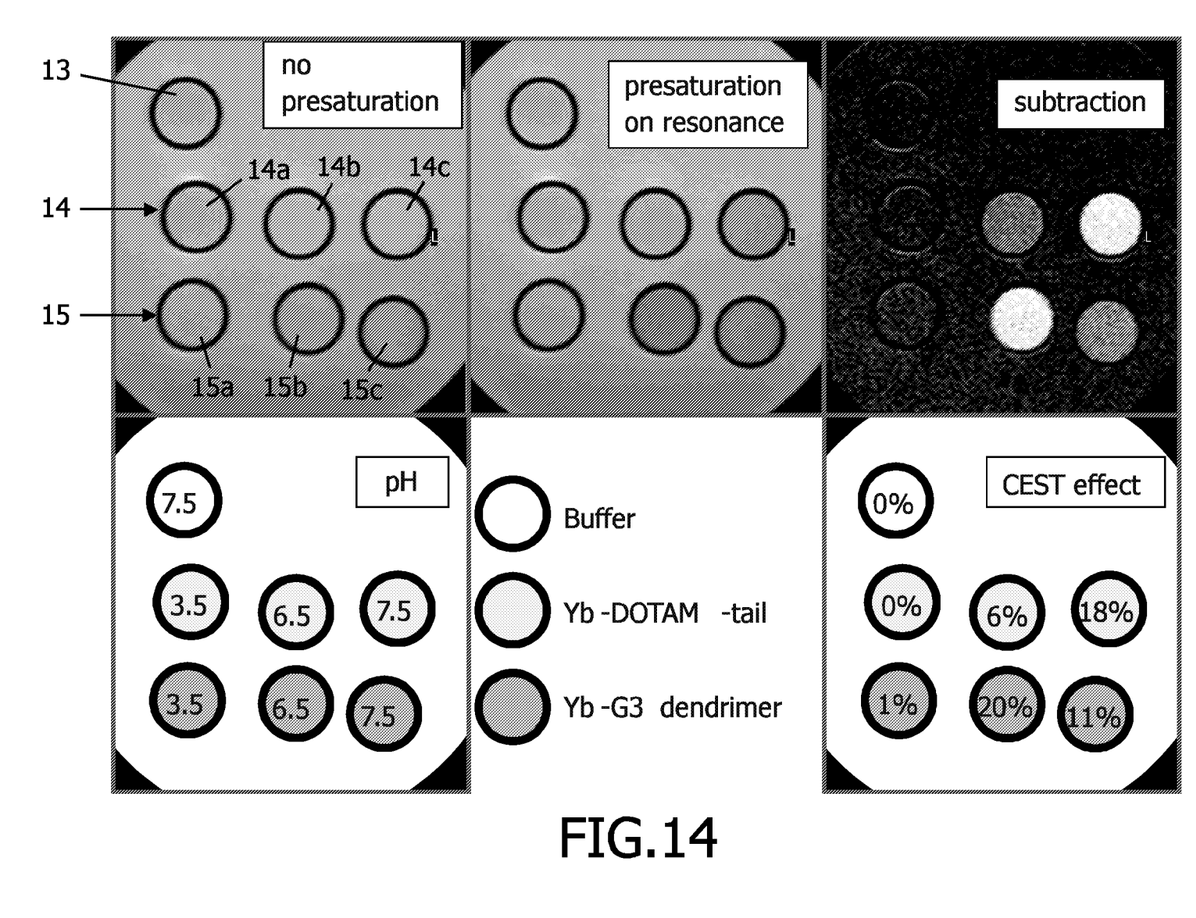
FIG. 14 shows TSE Proton Density Weighted images of a phantom comprising vials with solutions of only MOPS buffer (top vial), Yb-DOTAM-tail (14 mM, middle row) and Yb-DOTAM-G3 (0.9 mM, lower row) with MOPS buffer in water at various pH and 298K.

Imaging experiments were carried out on a Philips 3T human MRI scanner. A phantom comprising vials is illustrated in FIG. 14. The top vial 13 only comprises a MOPS buffer. The middle row of vials, indicated with reference number 14, comprises the Yb-DOTAM-tail complex (0.9 mM) at 3 different pH values, i.e. pH=3.5 (indicated by reference number 14a), pH=6.5 (indicated by reference number 14b) and pH=7.5 (indicated by reference number 14c). The lower row of vials, indicated by reference number 15, comprises the Yb-DOTAM-G3 complex at 3 different pH values, i.e. pH=3.5 (indicated by reference number 15a), pH=6.5 (indicated by reference number 15b) and pH=7.5 (indicated by reference number 15c). The phantom with the vials was placed in a beaker with physiological water. The concentration of Yb was the same in all vials 14a-c, 15a-c. Proton Density Weighted images were acquired in order to remove all contrast due to $T_1/T_2$ differences, since the aim in this experiment is to obtain contrast due to CEST. Indeed, the image without pre-saturation (FIG. 14, left image at the top) shows hardly any intensity differences. The magnetic field strength of the MRI scanner used is 3T (128 MHz), which is different from the magnetic field strength of the NMR spectrometer (7T, 300 MHz). Because of the difference in field strength, the exchangeable entities, in the example given amide protons, resonate at −1900 Hz on the Philips MRI scanner, whereas this is −5000 Hz on the Bruker NMR spectrometer. In FIG. 14, upon pre-saturation of the amide protons at −1900 Hz the intensity of the four most right vials is lower due to the occurrence of CEST (FIG. 14, middle image at the top). This can more clearly be seen in the right image at the top of FIG. 14, which is the difference between the left and the middle image. From FIG. 14 it can be seen that Yb-DOTAM-tail at pH 7.5 (14c) and Yb-DOTAM-G3 at pH 6.5 (15b) exhibit the largest CEST effect, which is in accordance with the CEST-pH curves illustrated in FIGS. 11 and 12. The maximum CEST effect is in this case ~20%. This is lower than obtained for the same solution at the Bruker NMR (7T) spectrometer used (~40%). The difference in CEST effect is due to the difference in pre-saturation pulse and not due to the field strength difference. The difference may be due to the different method used for the pre-saturation, i.e. 16 times 100 ms without pulsed field gradients instead of 300 times 5.0 ms with the combined use of pulsed field gradients. The CEST effect for Yb-DOTAM-G3 at pH 7.5 is ~11%, which is half of the value at pH 6.5. This is due to the shift of the amide proton resonance (see above). Because of this large difference between pH 6.5 and 7.5, Yb-DOTAM-G3 is a suitable contrast agent for pH mapping using CEST with good sensitivity thanks to the multiple paramagnetic ions per molecule.

It has to be understood that the above example of a CEST agent according to the invention is not limiting to the invention. Other molecules may also exhibit the benefits of the invention.

Figure 15:
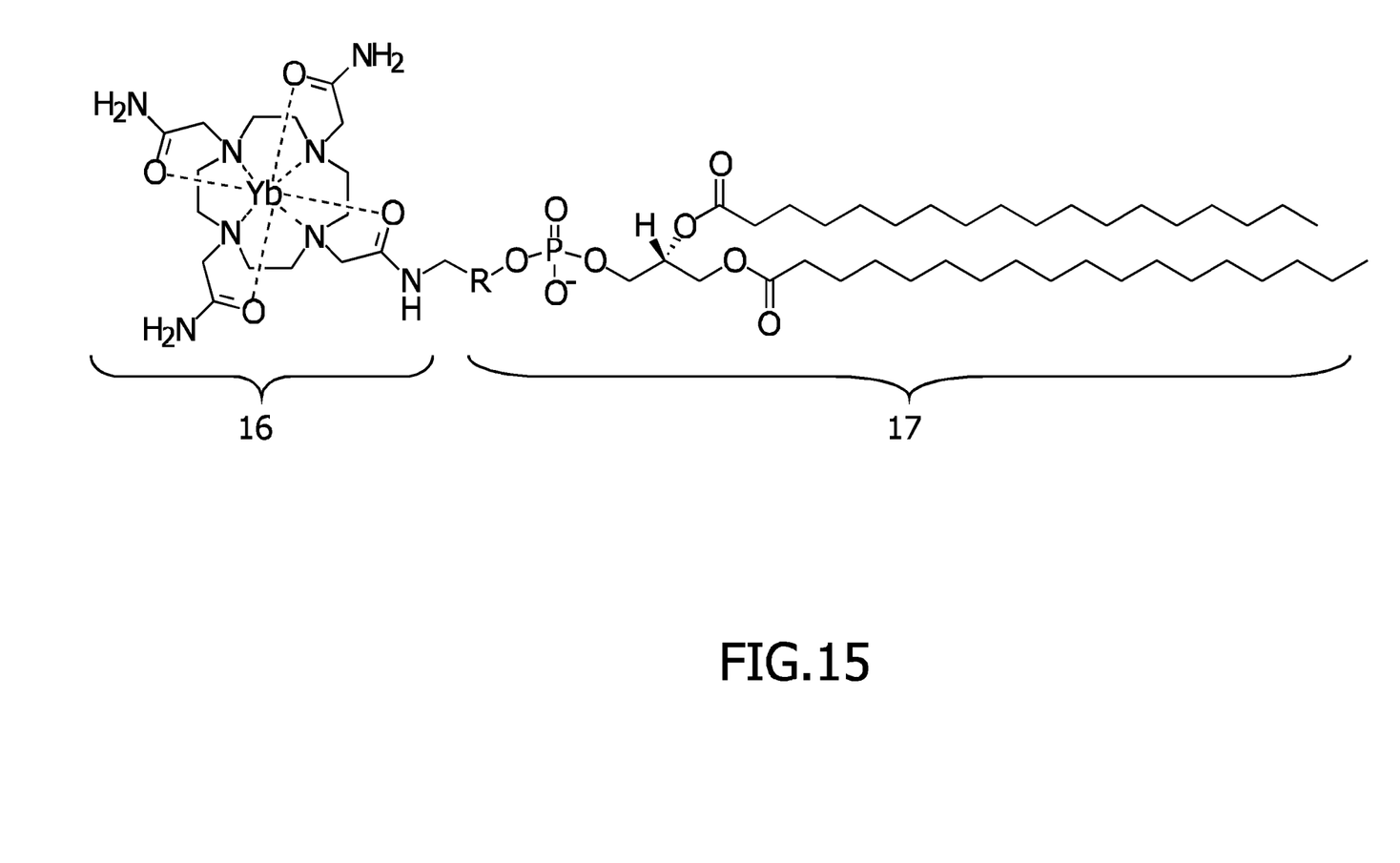
FIG. 15 illustrates a CEST agent according to an embodiment of the invention.

For example, a second embodiment of the invention provides a CEST agent which may comprise a complex that may be incorporated in a liposome in order to form a CEST agent according to the present invention. The complex comprises a CEST-active paramagnetic complex 16 and a phospholipid tail 17. The CEST-active paramagnetic complex 16 may comprise a paramagnetic ion such as a lanthanide ion, preferably $Yb^{3+}$ ionor all other suitable paramagnetic ions such as e.g. a transition metal ion, attached to a chelating agent. The paramagnetic complex comprises exchangeable entities which may preferably be exchangeable protons and which more preferably may be exchangeable amide protons. A specific example of such a CEST agent is illustrated in FIG. 15. The CEST-active paramagnetic complex 16 in this example may be Yb-DOTAM and may be attached to a phosphatidylcholine tail 17, more particularly a 1,2-distearoyl-sn-glycero-3-phosphocholine derivative tail. In this phosphatidylcholine tail 17, R may be C, $CH_2(OCH_2CH_2)_n$ or $CH_2(OCH_2CH_2)_n CONHCH_2CH_2$. Liposomes can contain up to 100 000 of these paramagnetic complexes, hence enabling a big improvement of the sensitivity of the MRI technique using such liposomes with paramagnetic complexes.

It is to be understood that although preferred embodiments, specific constructions and configurations, as well as materials, have been discussed herein for devices according to the present invention, various changes or modifications in form and detail may be made without departing from the scope and spirit of this invention.

The invention claimed is:

1. The MRI contrast agent, comprising:
    a carrier selected from the group consisting of liposomes, particles, and micelles, wherein the carrier includes a linking molecule comprising a phosphatidylcholine derivative;
    a plurality of CEST-active paramagnetic complexes linked to the carrier and including at least one exchangeable entity for enabling CEST;
    wherein at least one of the plurality of CEST-active paramagnetic complexes is covalently attached to the carrier via a nitrogen atom of the linking molecule, the linking molecule including an "R" group moiety covalently bonded to the nitrogen atom and a phosphate head group of the linking molecule, the "R" group moeity selected from the group consisting of: $CH_2(OCH_2CH_2)_n$, and $CH_2(OCH_2CH_2)_n CONHCH_2CH_2$.

2. The MRI contrast agent of claim 1, wherein at least one of the plurality of CEST-active paramagnetic complexes has a paramagnetic ion attached to a cheating ligand, and the plurality of CEST-active paramagnetic complexes includes at least two different CEST-active paramagnetic complexes attached to the carrier.

3. The MRI contrast agent according to claim 1, wherein:
    at least one of the CEST-active paramagnetic complexes has a first paramagnetic ion, a first chelating ligand, and at least one first exchangeable entity; and
    at least one of the CEST-active paramagnetic complexes has the second CEST-active paramagnetic complex having a second paramagnetic ion, a second chelating ligand, and at least one second exchangeable entity;
    wherein the first and second paramagnetic ions are different from each ether and first and second chelating ligands are different hem each other.

4. The MRI contrast agent of claim 3, wherein the first paramagnetic ion includes a first lanthanide ion and the second paramagnetic ion includes a second lanthanide ion different from the first lanthanide ion.

5. The MRI contrast agent of claim 3, wherein the first chelating ligand is a DOTAM-G1 derivative and the second chelating ligand is a DOTAM-G3 derivative.

6. The MRI contrast agent of claim 3, wherein the first and second CEST-active paramagnetic complexes include an asymmetric Yb-DOTAM complex.

7. The MRI contrast agent of claim 2, wherein one of the plurality of CEST-active paramagnetic complexes has a superparamagnetic iron oxide particle embedded in an organic material which includes the exchangeable entity.

8. The MRI contrast agent of claim 3, wherein the carrier has at least four surface groups to which the plurality of the CEST-active paramagnetic complexes are linked.

9. The MRI contrast agent of claim 1, wherein the carrier includes a linear polymer with a weight less than 20 kDa.

10. A CEST MRI contrast agent comprising:
    a common carrier selected from the group consisting of liposomes, particles, and micelles;
    a plurality of paramagnetic complexes, each including:
        a first chelating ligand linked to the common carrier;
        a second chelating ligand linked to the common carrier;
        a first and second paramagnetic ion;
        a first complex forming a first exchangeable entity between the first paramagnetic ion and the first chelating ligand;
        a second complex forming a second exchangeable entity between the second paramagnetic ion and the second chelating ligand;
        wherein the first and second chelating ligands are dendrimers of a different generation.

11. The MRI contrast agent of claim 10, wherein
    the first and second exchangable entities include amide protons; and
    the first and second chelating ligands include at least one of a DOTAM-G1 complex and a DOTAM-G3 complex.

12. The MRI contrast agent of claim 10, wherein:
    the first chelating ligand includes a DOTAM-G3 complex with 16 surface amino groups.

13. The MRI contrast agent of claim 10, wherein:
    the first and second chelating ligands are each covalently linked to a phospholipid included in the carrier, to incorporate at least one of the first and second chelating ligand into a shell of the carrier.

14. The MRI contrast agent of claim 10, wherein:
    the first and second chelating ligands are each covalently attached to a linker molecule comprising a phosphatidylcholine or phosphatidycholine derivative, the linker molecule including a phosphate head group for forming a hydrophilic shell of the liposome, micelle, or particle.

15. The MRI contrast agent of claim 1, wherein the carrier is a liposome configured to carry up to 100,000 CEST-active paramagnetic complexes.

* * * * *